（12） United States Patent
Pace et al.

(10) Patent No.: US 9,038,443 B1
(45) Date of Patent: May 26, 2015

(54) MICROFABRICATED RESONANT FLUID DENSITY AND VISCOSITY SENSOR

(71) Applicants: Maria Esther Pace, Discovery Bay, CA (US); Eric Anthony Perozziello, Discovery Bay, CA (US)

(72) Inventors: Maria Esther Pace, Discovery Bay, CA (US); Eric Anthony Perozziello, Discovery Bay, CA (US)

( * ) Notice: Subject to any disclaimer, the term of this patent is extended or adjusted under 35 U.S.C. 154(b) by 285 days.

(21) Appl. No.: 13/708,969

(22) Filed: Dec. 8, 2012

Related U.S. Application Data

(60) Provisional application No. 61/570,301, filed on Dec. 14, 2011.

(51) Int. Cl.
| | | |
|---|---|---|
| *G01H 13/00* | (2006.01) | |
| *G01N 11/10* | (2006.01) | |
| *G01N 9/00* | (2006.01) | |
| *G01N 29/036* | (2006.01) | |

(52) U.S. Cl.
CPC .............. *G01H 13/00* (2013.01); *G01N 11/10* (2013.01); *G01N 9/002* (2013.01); *G01N 29/036* (2013.01)

(58) Field of Classification Search
CPC ................................................... G01N 29/036
See application file for complete search history.

(56) References Cited

U.S. PATENT DOCUMENTS

| | | | | |
|---|---|---|---|---|
| 4,922,745 | A * | 5/1990 | Rudkin et al. | 73/32 A |
| 5,323,638 | A * | 6/1994 | Langdon | 73/32 A |
| 5,533,381 | A * | 7/1996 | Seale | 73/19.03 |
| 5,602,333 | A * | 2/1997 | Larrabee et al. | 73/149 |
| 5,872,309 | A * | 2/1999 | Pinter | 73/49.3 |
| 5,877,416 | A * | 3/1999 | Kapartis | 73/170.13 |
| 6,023,961 | A * | 2/2000 | Discenzo et al. | 73/54.01 |
| 6,206,290 | B1 * | 3/2001 | Giebel et al. | 235/462.36 |
| 6,269,686 | B1 * | 8/2001 | Hahn et al. | 73/54.24 |
| 6,336,353 | B2 * | 1/2002 | Matsiev et al. | 73/24.06 |
| 7,329,932 | B2 * | 2/2008 | DeNatale et al. | 257/417 |
| 7,874,199 | B2 | 1/2011 | Chaudoreille | |
| 8,020,432 | B1 * | 9/2011 | Ballato | 73/54.41 |
| 8,210,030 | B2 * | 7/2012 | Djakov et al. | 73/54.27 |
| 8,732,938 | B2 * | 5/2014 | Kolosov et al. | 29/594 |
| 2008/0197430 | A1 * | 8/2008 | Aigner et al. | 257/414 |
| 2008/0257036 | A1 * | 10/2008 | Chaudoreille et al. | 73/32 A |
| 2010/0121583 | A1 * | 5/2010 | Abbott et al. | 702/50 |

* cited by examiner

*Primary Examiner* — Charlie Y Peng

(57) ABSTRACT

Determination of fluid properties is important in a variety of research and industrial applications. Real-time measurements in operating fluidic systems are performed for monitoring, diagnosis, and feedback-control. A simplified, microfabricated resonant sensor for separate density and viscosity measurements of a fluid with a common sensor is disclosed. The sensor is micron-scale, so as to produce a minimum of perturbation to the fluid under test, and may be arrayed to probe viscosity and density across a flowstream or vessel. Measurement is performed at resonance peaks, and geometry or operating conditions of sensor are varied to produce different resonance responses useful for separate sensing of density and viscosity of a fluid. Another embodiment includes a method for reducing quiescent in-plate elastic strain in a plate or membrane so as to allow bending-stiffness dominated behavior of a resonator.

18 Claims, 10 Drawing Sheets

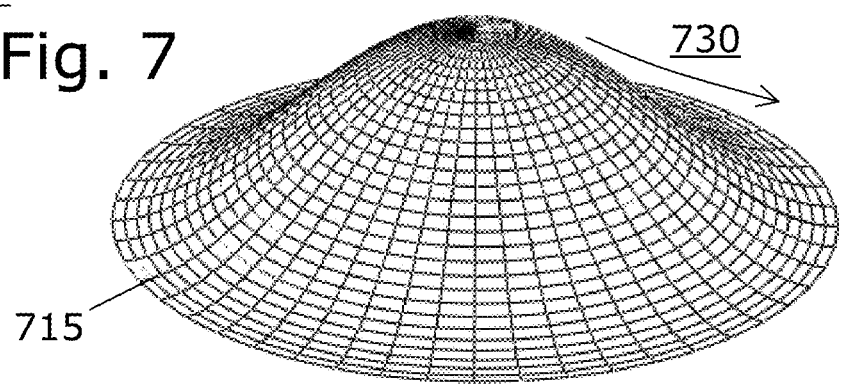
Fig. 7    730
715
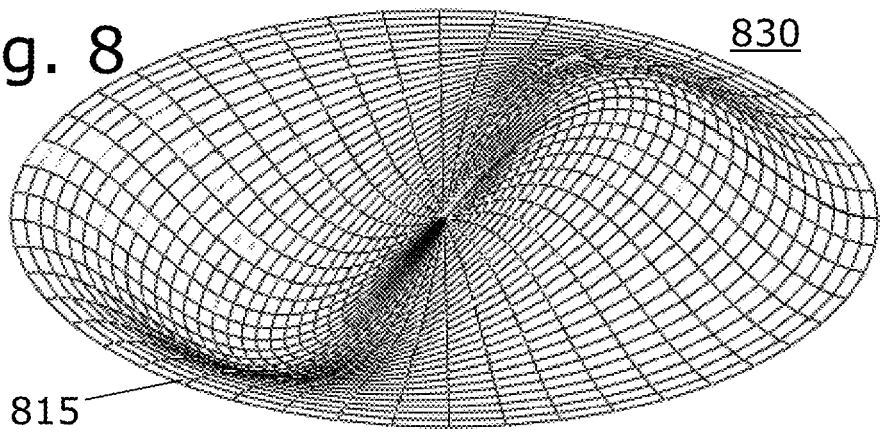
Fig. 8    830
815
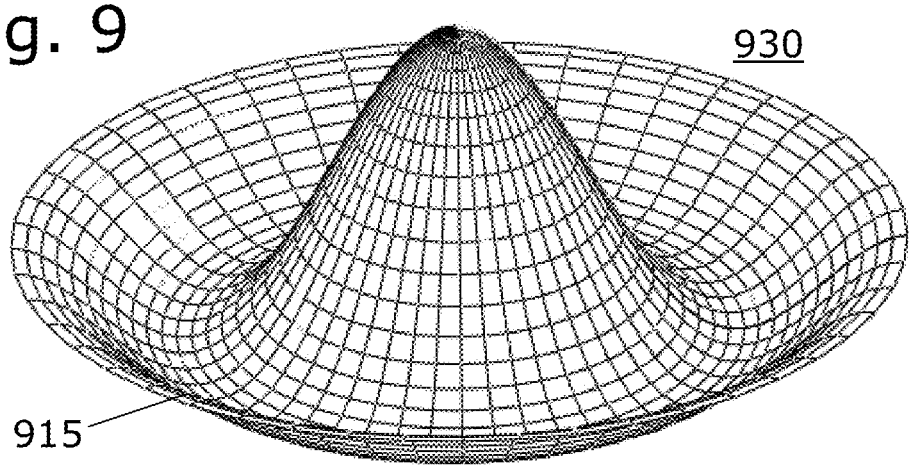
Fig. 9    930
915

MICROFABRICATED RESONANT FLUID DENSITY AND VISCOSITY SENSOR

This application claims the benefit of U.S. Provisional Application No. 61/570,301, filed Dec. 14, 2011.

FIELD OF THE INVENTION

The field of the present invention relates generally to fluidic sensors. In particular, the field of the invention relates to microfabricated and nanofabricated resonant fluid sensors.

BACKGROUND

In any application where fluids are used, sensors are often employed to measure properties of the fluid, such applications including aviation, fluid delivery, heat exchange/refrigeration, semiconductor processing, fluid identification and detection, medical and bio-diagnostics. Quantities measured include temperature, viscosity, density, pressure, flow rate, molecular composition and state of matter. Sensors are transducers, which convert the property being measured into another useful form, often electrical, for recording, observing and controlling. In order to make a useful sensor, the device must respond to a physical input change by producing an output change. The degree to which the output changes with respect to the input change is termed the sensitivity of the sensor.

DEFINITIONS

Resonators are devices that oscillate at a natural, or resonant frequency, two simple examples being a pendulum under the influence of gravity and a mass-spring system. In either case, a balance of forces exists at all points in time. The natural rate at which these forces trade off determines the value of the resonant frequency. A string, plate or beam is considered a continuous system, wherein the spring and mass are not discrete, but continuously distributed throughout a volume. It is generally stated that the resonant frequency of a mechanical system is proportional to the square root of the stiffness-to-mass ratio.

Microfabrication, such as the process used to make integrated circuits, can be employed to make resonators. Advantages to microfabrication are numerous, including economic advantages and process control, but in the case of sensors, micron dimensions generally mean fast sensor response times on the order of microseconds. The smaller market of micro-electro-mechanical systems (MEMS) borrows economy-of-scale from the much larger semiconductor market in order to make sensors which are higher performance and lower in cost than otherwise possible. Microfabrication also allows the repetition of devices having design variations on a single substrate with substantially no added cost or complexity in manufacture. For instance, the radius of a microfabricated sensor element need not be optimized for one operating condition because multiple radii can be replicated therein to encompass a larger operating range with virtually no disadvantage other than a slightly larger chip. Multiple elements operating synchronously, with common, or separate circuitry are added at almost no cost. Close coupling of sensors to their drive circuitry also provides a performance advantage not available in conventional discrete systems. Ideally, a sensor should not perturb the system it seeks to measure. Small sensors provide lower disturbance to the system being measured, consume less power and allow for lower driving voltages.

Graphene is a carbon-based nano-material that is actively being researched. Much of the literature is focused on very high electron mobility (electronic conduction). Graphene is a single sheet of carbon atoms arranged in a hexagonal crystalline pattern and, like its 3D carbon parent diamond, is very strong. Graphene's young's modulus is reported at approximately 1 Terapascal, and it is has a thickness of approximately 0.335 nanometer. Despite this infinitesimal thickness, graphene is highly electrically conducting and impermeable to gasses and liquids. Graphene is also resilient at high temperatures and in many harsh environments. Chemical-Vapor-Deposited graphene on various substrate sheets is available from, for instance, https://graphene-supermarket.com/.

DISCUSSION OF PRIOR ART

Resonators have been extensively employed in the measurement of fluid properties.

U.S. Pat. No. 7,329,932B2 discloses a microfabricated viscosity sensor and method wherein a suspended, perforated plate is forced toward a substrate, with the measured fluid disposed in the gap between, and the motion in response to a force is sensed. The fluid is thereby squeezed out from the gap and out of the perforations. This design maximizes shear forces of the fluid, and is therefore is sensitive to viscosity of the fluid.

U.S. Pat. No. 8,020,432B1 discloses a microfabricated resonant viscometer that relies on a similar motion of the fluid under test. This sensor is operated in resonance to detect changes in the viscosity, and further comprises a moving boundary to change the gap dynamically in order to tune the sensor to the specific fluid under test, thus increasing the dynamic range of the sensor. They teach that "there is no reliable way to measure the quantities $\eta$ (viscosity) and $\rho$ (mass density) separately."

Both U.S. Pat. No. 8,020,432B1 and U.S. Pat. No. 7,329,932B2 require small gaps exposed to the fluid ambient, and are thus sensitive to small particulate contamination from the fluid stream. These sensors accomplish the measurement of viscosity, but not density. It would be desirable to obtain density from the same sensor. It is further desirable to have a sensor that is not sensitive to particles lodging in small gaps. In a microfabrication process where all steps in the process must be applied to all devices on a substrate, it is highly desirable that one sensor design, with only planar geometry changes, serve the purpose of measuring both quantities. It is also desirable that this be accomplished by adding no (or relatively few) steps to the fabrication process to achieve a device that can measure both quantities.

U.S. Pat. No. 6,269,686B1 discloses a microfabricated resonant cantilever for measuring both density and viscosity, teaching that a shift in resonant frequency indicates the fluid density and measurement of the width of the resonance curve supplies the viscosity information. In other words, they measure the quality factor, Q, to obtain the fluid's viscosity—a measure of the energy loss due to damping of the resonant system. As is discussed in further detail below, it is desirable to eliminate the measurement of Q in determining the fluid's viscosity.

U.S. Pat. No. 7,874,199B2 discloses a viscosity and density sensor that uses a resonant frequency measurement of a cantilever to determine viscosity and density. As disclosed, this sensor is not readily amenable to microfabrication. They require that the resonance characteristics be determined at two resonant frequencies, including both the frequency of peak resonance and the Quality factor, Q. The quality factor is a measure of the frequency-breadth of the resonant peak and is indicative of the energy dissipated in a resonant system.

A key element of the invention disclosed in U.S. Pat. No. 7,874,199B2 is to "replace the evaluation of (constants) through independent measurement of temperature and pressure and the knowledge of the beam material properties by using at least two vibration modes of a single vibrating element (or two vibrating beams of the same material) having different fitting parameters." In other words, viscosity and density can be obtained from a single frequency and quality factor measurement but a key reason for using two frequencies/modes/elements is to determine the correction factor for the resonator. Fitting parameters are further obtained by calibration with known reference fluids in order to correlate resonance frequency and quality factor with viscosity and density. While calibration of any sensor usually improves accuracy, it would be desirable to have a sensor for which calibration with known reference fluids is optional.

Based on the determined resonant frequency and the quality factor and a fitting model for the particular resonating element used, the density and viscosity can be calculated. U.S. Pat. No. 7,874,199B2 requires the determination of the quality factor at each resonant frequency used. Because of the extra circuitry required, calibrations required, inaccuracies and time required for such measurements, as described below, it would be desirable to have a method wherein the determination of the quality factor of a resonator is not required to sense both density and viscosity.

U.S. Pat. No. 7,874,199B2 selects two modes with the first resonant frequency highly sensitive to density, moving a volume of fluid, and the second resonant frequency sensitive to the damping effect, shearing a surrounding fluid. They further state that "As the resonating element vibrates, some of the surrounding fluid is displaced. The effective mass of the resonating element is increased by an amount determined by the volume and density of fluid entrained by the moving section." This is the basis of most resonant mass and density sensors—a measured increase in the inertia of a vibrating element. They further state, "As the resonating element vibrates in the fluid, the resonating element drags through the fluid in shear. Consequently, the vibration is dependent upon the resistance to the shear of the fluid, hence a viscometer is provided." As will be explained later, it would be advantageous to avoid measurement of viscous drag (through measurement of Q) as the mechanism for viscosity determination in a resonant sensor.

U.S. Pat. No. 7,874,199B2 discloses a measurement technique that is based on the succession of an excitation phase followed by a waiting phase and a detection phase. After a waiting phase, the decaying signal due to oscillation amortization of the resonating element in the fluid is measured. The detection duration is a tradeoff between computing complexity and measurement accuracy. They state as an example "measurement and calculation can be performed in less than 1 second," however they do not provide a corresponding sensor accuracy value with this example. If a sensor is used in a feedback loop, a sensor delay on the order of 1 second would provide unacceptable control if the gain of the feedback loop is high, for instance in a process gas controller. Depending on the frequency bandwidth of the sensor, multiple excitations may be needed to find the resonance(s). Measurement at multiple resonances on a single device would require switching frequencies, and an associated waiting phase and detection duration with each such frequency measurement. As the sensor disclosed is not easily adaptable to microfabrication, the cost of adding sensor elements in an array is nearly linear with the number of sensor elements. The decay method for determining Q is not well suited for low values of Q (ie: high viscosity). What is desired is a sensor that could alter its resonance response as a continuum of frequencies so that the sensor electronics can remain locked in resonance, rather than providing only discrete built-in resonance modes that may require searching for resonance peaks.

A further limitation in U.S. Pat. No. 7,874,199B2 is that the embodiments rendered therein are not readily adapted to microfabrication. Microfabricated sensors are smaller, and therefore disrupt the working fluid less. They cost less, and are easier to integrate with electronics, and performance benefits can be realized by miniaturization. As will be appreciated by those skilled in the art, microfabrication would be advantageous for numerous applications.

U.S. Pat. No. 5,323,638 discloses a resonant tine structure. They teach the measurement of multiple frequencies on either side of resonance to estimate Q, similar to U.S. Pat. No. 7,874,199B2, for the determination of viscosity. They calculate a damping factor followed by an approximation for viscosity.

U.S. Pat. No. 4,922,745 discloses a resonant tine sensor, and teach the shaping of the tines to entrain more fluid with the tine motion, thus responsiveness to density change is greater as the amount of entrained fluid increases relative to the mass of the tines. As an example, they cite re-entrant facing surfaces forming a "C" shape. It will be obvious to those skilled in the art of microfabrication that such a shape is non-trivial to produce by that method, so this aspect of the design and teaching of U.S. Pat. No. 4,922,745 is impractical for microfabrication methods. They further teach that an opposite design, entraining less volume but having a large surface area for drag, (and hence viscosity) when vibrated in their plane of elongation provides a liquid viscometer. In other words, minimize the entrained mass and maximize surface drag for maximal viscosity sensitivity for a liquid viscometer, which is equivalent to maximally affecting Q with changes in viscosity. Thus, U.S. Pat. No. 4,922,745 teaches the entrainment of more fluid for a density measurement, and the entrainment of less fluid for a viscosity measurement.

Accordingly, in order to overcome the shortcomings and disadvantages of conventional technologies, what is needed is a sensor which is able to measure the density and viscosity of a fluid in a manner that is rapid, microfabricatable, insensitive to particulate contamination, and simple, requiring only resonance peaks to be determined, with the ability to remain locked-in to resonance as the resonant frequency is changed.

SUMMARY

In order to overcome the above-discussed disadvantages of conventional fluidic sensors, one aspect of the present invention utilizes the fact that different resonant frequencies, mode shapes, and geometries of resonators respond differently to a fluid's density and viscosity. A further aspect is that a thin plate in resonance can act as a membrane (having substantially no bending stiffness) or a plate (having substantially no tension) depending on the geometry and in-plane elastic strain imparted, thereby providing a different and separate response to interaction with a fluid having different viscosity or density and can be provided using the methods and teachings herein.

Another aspect of the present invention is that microfabrication techniques can produce very large dimensional aspect ratio structures, which enhance the aforementioned features of the invention. In the context of the present invention, aspect ratio is defined as the ratio of the in-plane dimension (radius of a disk, length of a beam) to the thickness of the plate.

Aspect ratios of greater than 1000:1 are achievable, which renders the plate-to-membrane transition significant in magnitude, and useful for sensing. Small, microfabricated dimensions allow a fast sensor response. Frequencies can be in the megahertz to gigahertz range, allowing for very fast tracking of a rapidly changing resonant frequency.

Inertia Versus Energy Loss

Many references cited rely on the calculation of the quality factor, resonant peak width, energy lost due to viscous damping, viscous drag, etc, which all relate to the same physical quantity. The viscosity, or proportionality constant between a fluid's rate of shear strain and shear stress, causes energy loss in the resonating systems, which manifests as a broadening of the spectral response around the resonant frequency. An additional effect of the viscosity, apart from the shear resistance leading to lower quality factor, Q (a measurement of energy dissipation), is a change in the mass entrained due to viscosity added to the entrained mass for the inviscid case. The magnitude of this additional entrained mass being dependent on the details of the resonator, and as will be described later, is variable and controllable, and proportional to the numerical value of the viscosity. This effect does not represent an energy loss to the system, or a dissipative quantity, and is therefore not represented in Q or in the amplitude decay of a resonance. An aspect of the present invention makes use of this additional entrained mass being proportional to viscosity, and seeks to optimize the sensor's response, under certain cases, to this mass. Megahertz resonant frequencies improve the sensor's response to inertial mass rather than the dissipative damping.

In an inviscid case, the effect of the mass of the fluid is inversely proportional to the acceleration of the resonating element, thus increasing the inertial term of the equation of motion. The fluid is free to move in a direction normal to the plane of the resonating element, or in a direction tangential to the plane of the resonating element to accommodate the oscillatory motion. That is, the fluid can follow the oscillation of the resonator (adding to its effective mass) or it can slosh tangentially to effectively move out of the way of the moving resonator. This is consistent with most methods taught and is generally the basis for resonant density sensing.

In the case of a viscous fluid, the fluid can no longer (completely) freely move tangential to the direction of oscillation to avoid direct entrainment in the motion of the oscillator. As it is generally assumed that there is a no-slip condition at the solid-fluid interface at the resonator surface, viscosity dictates the permissible strain rate, or tangential motion of the fluid. Thus, the fluid is constrained, at least partially, in the tangential direction, there being a viscous force opposing tangential motion. This is partially energy-dissipative (as recognized in those references using Q for viscosity calculation), but there is a non-dissipative component that requires the inertia of the fluid that is entrained by the motion of the resonator to be greater than in the case of an inviscid fluid. The magnitude of the effect of the viscosity (in comparison to the effect of the density) depends on the details of the conditions of the motion and geometry of the resonator (thickness, lateral dimension/radius, operating mode, frequency). This effect is separate from the dissipative effect, quantified by Q, of the resonator.

An Electrical Analogy

This concept can be better understood with an electrical analogy. A resonant electrical circuit includes a Resistor (R), an Inductor (L) and a Capacitor (C). It is well known that the driven or forced resonant frequency is $\sim(LC)^{-1/2}$. The effect of the resistance, R, is to broaden the resonance peak. A larger numerical value of R produces a wider shape resonance peak, thus L,C can be obtained from measurement of the resonant frequency while R can be obtained from measurement of the shape of the peak, in other words, Q. The mechanical resonator employs a similar equation of motion with R substituted with a viscous term, L substituted with a mass term, and 1/C substituted with a stiffness term. Thus, in the simplest case of a mechanical resonator, the resonant frequency is $\sim$(stiffness/mass)$^{1/2}$, a well-known elementary relationship. Obtaining the viscosity from Q of a mechanical resonator is directly analogous to obtaining R (electrical resistance) from the measured Q of a driven RLC circuit. If the RLC circuit is not actively driven at resonance, then the resonant frequency does depend on R, the so-called damped resonant frequency. It is possible to obtain R from the damped resonant frequency, which is a measurement of the damping effect.

It is not analogous, however, that a second effect, in the mechanical case, is that the viscosity also increases the inertial term (for reasons discussed above related to viscous restraint of tangential fluid motion). The magnitude of this can be exploited to enhance sensor sensitivity, and also functionality. Therefore, the measurement of Q is unnecessary if the driven mechanical resonator is properly designed.

Plate and Membrane Behavior

Elastic theory of plates and membranes is generally employed in the calculation of mechanical resonance. A seminal reference on the subject of elastic theory is provided in Timoshenko and Goodier, "*Theory of Elasticity*," McGraw-Hill Book Company, 2$^{nd}$ Ed. 1951 and the application to vibratory analysis is provided in Timoshenko and Young., "*Vibration Problems in Engineering*," D. Van Nostrand Company, 4$^{th}$ Ed. 1973, both of which are incorporated herein by reference.

In the aforementioned references, the use of the word "plate" generally refers to a substantially flat, flexible body that is resistant to bending only. That is to say that a plate, in this context, possesses an equilibrium-restoring force that acts throughout its volume to provide a bending moment toward equilibrium if it is perturbed from that equilibrium. The magnitude of the restoring force is known as the bending stiffness or flexural rigidity.

The word "membrane" is used to generally in these references to refer to a flexible body that has no bending stiffness (in contrast to the case of a plate), but is stretched such that the in-plane elastic stress maintains the shape of the body, and any perturbation to that equilibrium shape produces a restoring force through the in-plane elastic stress/strain. It should be noted that the equilibrium shape may still retain a quiescent in-plane strain in equilibrium, but that in-plane strain is minimized in the equilibrium position.

In the context of the present invention, the word "plate" is used to describe a substantially flat, thin body, not limited to only bending moments for equilibrium restoration. In other words, in the context of the present invention, the word "plate" is also inclusive of a "membrane," and may have an equilibrium restoring force dominated by bending stiffness, or in-plane stresses, or a combination of these.

An aspect of the present invention uses variable in-plane elastic strain in a plate to cause that plate to transition gradually from having a bending stiffness-dominated to an in-plane strain-dominated restoring force. The resonant response of the sensor to this transition is advantageous in the separate determination of physical quantities viscosity and density.

If a plate is supported on its ends or periphery (for instance, a disk suspended over a round cavity, or a beam suspended between end supports) the in-plane strain may be increased by deflecting the plate either upward or downward, normal to its plane. This may be accomplished by applying a quasi-static (DC) voltage (potential) between the plate and a nearby second plane. The attractive electrostatic (coulombic) force deflects the plate in the direction of the second plane, thereby stretching and adding in-plane tension to the plate, deforming to a new equilibrium position. This in-plane tension increases the resonant frequency. Small oscillations produce a slight increase in the in-plane elastic strain, but these are considered sufficiently small that the tension is considered as constant in the equations that follow. The in-plane elastic strain is substantially linearly related to the tension through Young's Modulus of the plate material and plate dimensions.

Equation of Motion

For the case of a circular plate, the equation of motion, including in-plane strain and inertial loading is $$D \cdot \nabla^4 Y(r, \theta, t) - T \cdot \nabla^2 Y(r, \theta, t) + \beta \cdot \frac{\partial^2}{\partial t^2} Y(r, \theta, t) + c \cdot \frac{\partial}{\partial t} Y(r, \theta, t) = Q \quad (1)$$

where $\nabla$ is the vector differential operator, $\beta$ represents the inertia of the system, $Y(r,\theta,t)$ is the function representing the displacement of the plate as a function of time, t, and r, $\theta$, the in-plane coordinates. Q is a forcing function that drives or maintains the resonator in resonance and c is a viscous damping coefficient. T is the in-plane tension (proportional to strain), and D is the flexural rigidity, given by:

$$D = \frac{E \cdot h^3}{12 \cdot (1 - v^2)} \quad (2)$$

where E is young's modulus of the resonator plate material, h is the height, or thickness, of the plate, and v is poisson's ratio of the resonator plate material (not to be confused with kinematic viscosity, which uses the same symbol). Similar equations exist for other geometries than a disk.

The solution to this equation is often only obtainable by numerical methods, depending on the boundary conditions at the periphery of the plate. For the present case, the boundary conditions of interest are usually a "clamped" boundary, such that $Y(r=a,\theta,t)=0$ and $$\frac{\partial}{\partial r} Y(r = a, \theta, t) = 0$$

(where a is the radius of the suspended portion of the plate), indicating that at the plate boundary (r=a) the plate doesn't displace in a normal direction, and must also be horizontal at the boundary indicating that the clamped plate is restrained from bending at the boundary. Elastic theory requires that the amplitude of vibration be small compared to the lateral dimension of the plate.

Inertial Mass

The form of $\beta$ depends on the surrounding ambient. If the resonator is operating in vacuum, then $\beta$ is simply the density of the material, $\rho_{plate}$, plate from which the resonating plate is fabricated.

If the resonator operates in an inviscid fluid, $\beta$ further contains a term proportional to the aspect ratio of the plate and the density of the fluid, $\rho_{fluid}$.

$$\beta \sim \rho_{plate} + K_1 \frac{a}{h} \cdot \rho_{fluid}$$

In the case of a viscid fluid, $\beta$ further contains a term proportional to the square root of fluid density and viscosity ($\mu$), and inversely proportional to plate thickness and the square root of the resonant frequency, $\omega$.

$$\beta \sim \rho_{plate} + K_1 \frac{a}{h} \cdot \rho_{fluid} + K_2 \frac{1}{h} \cdot \sqrt{\frac{\rho_{fluid} \cdot \mu}{\omega}}$$

The constants ($K_2$ and $K_1$) in the above calculations depend only on the mode of vibration of the resonator. It is therefore desired, in the present invention, to entrain more mass due to the viscosity, under certain conditions where the measurement seeks to find viscosity. An aspect of the present invention is that different modes of vibration can be selected to improve the sensitivity of the sensor to either viscosity or density.

Modes and Geometry

In the case of mode calculation, the mode is determined by the eigenvalues of the solution to equation (1). For a disk, there are radial as well as circumferential modes (which may combine to form hybrid radial/circumferential modes) of vibration. Since the solutions for a disk are Bessel functions, the radial mode is determined by the order of the Bessel functions used in the solution and a $\cos(\theta)$ term. The circumferential mode is determined by the particular root of those Bessel functions chosen to satisfy the equation.

In accordance with another aspect of the present invention, the constants depend only on mode, so calibration is unnecessary. Calibration may be employed to fine-tune the sensor, or more accurately null manufacturing variations (which are small due to microfabrication with pure materials).

A further aspect of the invention is that the sensor sensitivity can be improved or enhanced by changing the thickness of the plate if the plate's motion is dominated by bending moments, and the sensor sensitivity can be enhanced by changing the in-plane dimension (radius, length) of the plate if the plate's motion is dominated by in-plane strain.

The solution to the equation of motion (1) with a viscid fluid is necessarily numerical in nature because the equation becomes transcendental. Such solutions can be tabulated into a database that contains frequency response tables for all geometries, operating conditions, tension and modes. Alternatively, solutions can be iteratively solved by a computer in real time.

Exploitation of the viscosity measurement requires optimization of the sensor element to discern the difference between the inviscid entrained mass and the viscous entrained mass. A high aspect ratio plate, which can transition to a membrane by the addition of in-plane strain is one aspect of the present invention. Use of higher modes of vibration is another aspect of the present invention, as the tangential motion of the fluid is more constrained in the case of a viscous fluid. An aspect of the present invention seeks to entrain more fluid mass for an accurate viscosity measurement. This is especially important for gasses, which typically have low viscosities. Because the present invention relies only on resonant frequencies, and not Q or shapes of a resonance response, small differences may be resolved for accurate determination of the fluidic properties.

Reference Sensor

In accordance with another aspect of the present invention, a reference sensor may be included on the same substrate, which does not interact mechanically with the fluid under test. If the reference sensor is operated in vacuum, or in a reference fluid that has significantly lower density and viscosity, then the effect of the fluid under test on resonant frequency of an identical sensor can be more accurately determined. The reference sensor will share the same ambient conditions (for instance, temperature) excepting the mechanical interaction with the fluid under test. A vacuum reference sensor self-calibrates the tension versus DC potential relationship, and allows cancellation of common-mode noise.

Microfabrication

Because the present invention is designed to be microfabricatable, it has numerous advantages. In addition to the general advantages cited in the introduction, the present invention, having micron-scale dimensions, can be placed in a fluidic apparatus or flow stream with virtually no detectable perturbation to the fluid under test. This is in contrast to large tuning fork structures and other non-microfabricated structures. Owing to this small size and relatively insignificant disturbance to a system, many sensors can be arrayed throughout a fluidic system or flow path to obtain a profile, distribution or map of fluidic properties in real-time.

The sensor also consumes very low power, owing to its small size and low dissipation design. Many prior art references use piezoelectric drive mechanisms, which require high voltage, even lethal voltages. The present invention, owing to capacitive drive in one embodiment and small dimensions, requires only the use of low voltages safe for humans. Furthermore, the sensor is easily integrated with electronics on the same substrate if substrate is a semiconductor. Having electronics in close proximity to the sensor drastically reduces noise introduced by external factors, as is known to those skilled in the art of MEMS sensors.

The fabrication of the present invention is simple, with only a few parts, and as few as one moving part. The microfabrication sequence requires no specialized equipment other than that already available in a well-equipped MEMS or semiconductor fab. In accordance with an aspect of the present invention, the surface of the sensor element is planar, with no gaps. Thus, the present invention is insensitive to particulate contamination contained in the fluid under test.

Not all designs are amenable to microfabrication. In other words, the process of making a micro-sensor is not as simple as shrinking dimensions of a conventional sensor to a micron scale, because microfabrication uses special techniques not common with conventional manufacturing, such as thin-film techniques. The present invention is designed to be microfabricatable with only ordinary tools and skills.

BRIEF DESCRIPTION OF THE DRAWINGS

These and other features, aspects and advantages of the present invention may be appreciated from the following detailed description and appended claims together with the accompanying drawings in which:

FIG. 7 shows a disk-type resonator plate deflected in the fundamental mode of vibration;

FIG. 8 shows a disk-type resonator plate deflected in the first radial mode of vibration;

FIG. 9 shows a disk-type resonator plate deflected in a first, non-fundamental circumferential mode of vibration;

DETAILED DESCRIPTION

Figure 1:
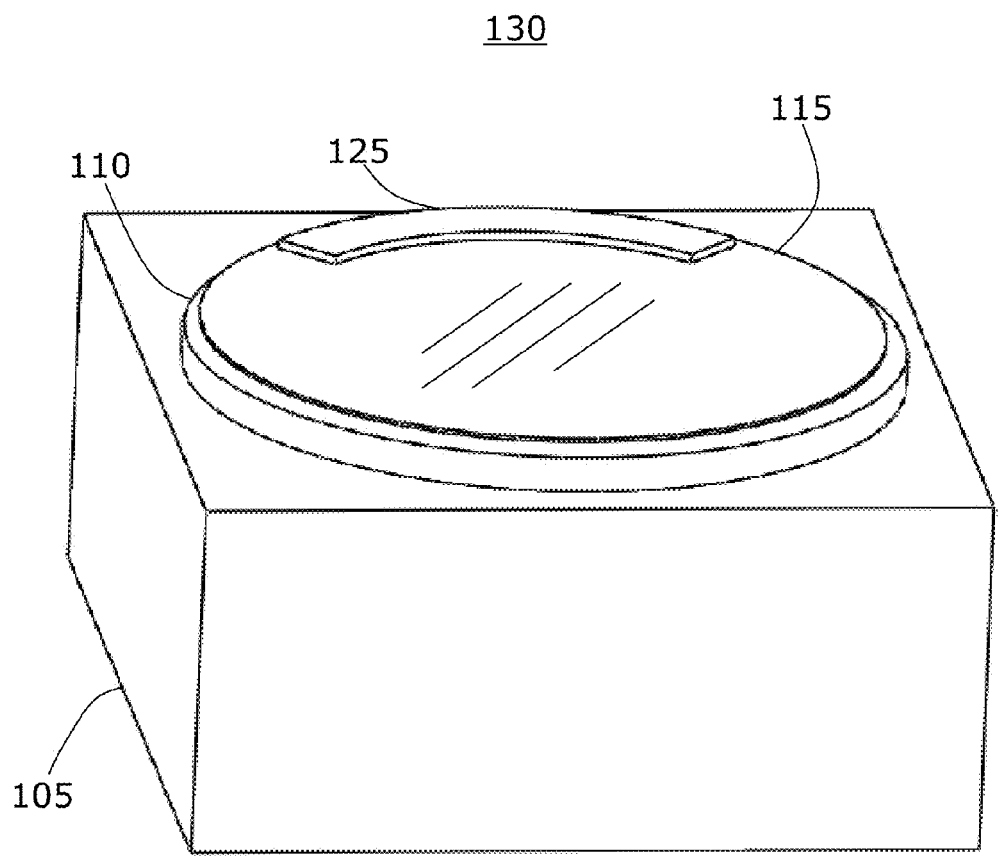
FIG. 1 is a perspective view of an embodiment of the present invention having a disk-shaped resonator.

One aspect of the present invention is a microfabricated resonant sensor, operated at a resonant frequency, which may be variable. A perspective view of the preferred embodiment is shown in FIG. 1. A substrate 105, which may contain drive electronics and detection electronics, having a substantially flat top or principal surface is provided. A support 110 is placed onto principal surface of substrate 105. A thin plate 115, which may behave as a plate with substantial bending stiffness, or as a membrane having substantial in-plane elastic strain, or a combination of these is positioned onto support 110 to form a suspended resonant structure that is free to oscillate in a direction normal to the plane of thin plate 115. A top electrode 125 is formed in electrical contact with thin plate 115.

A fluid 130 under test, which generally surrounds the sensor is exposed to, and is in communication with thin plate 115.

Figure 2:
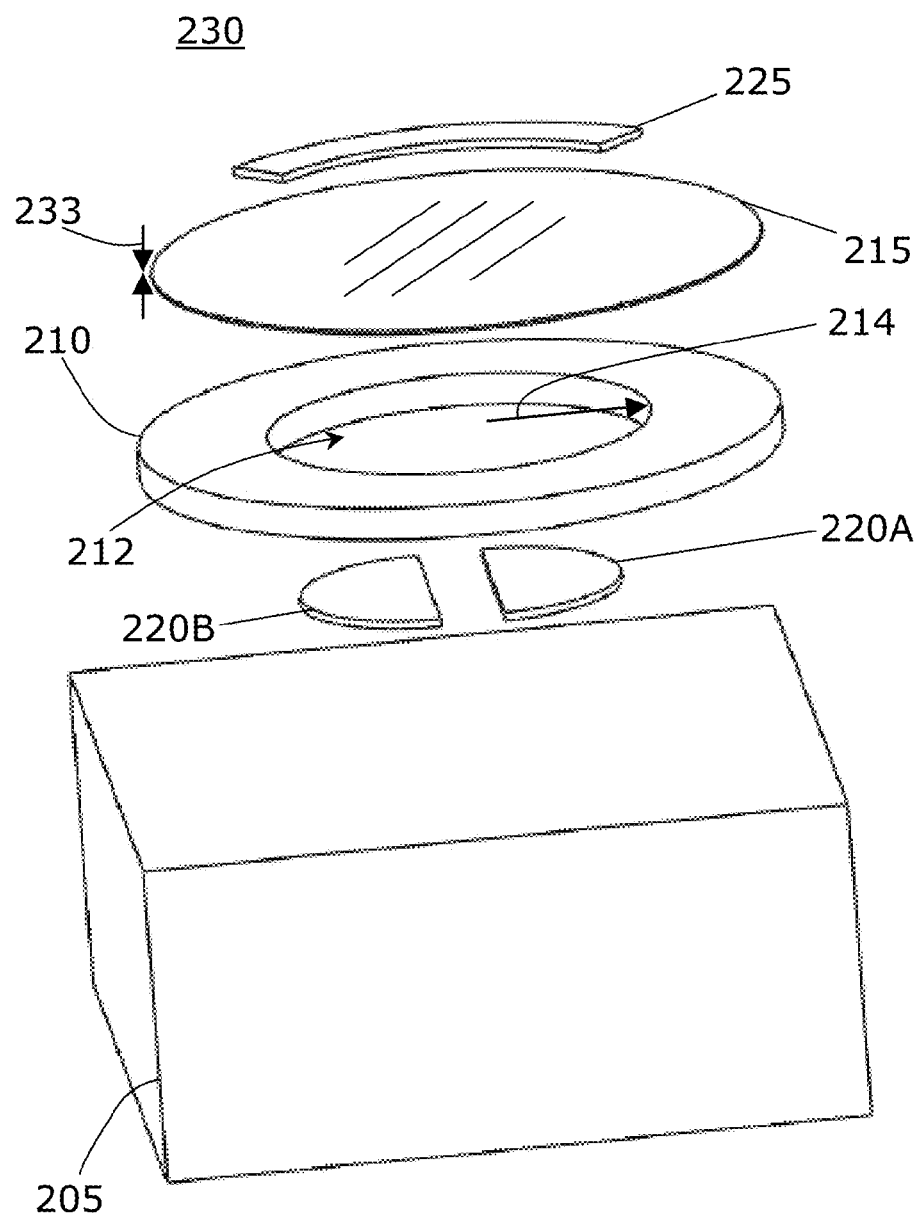
FIG. 2 is an exploded view of an embodiment of the present invention having a disk shaped resonator showing a segmented lower electrode.

An exploded perspective view of the preferred embodiment is shown in FIG. 2. Substrate 205 has support 210 placed on top or principal surface of substrate 205. Support 210 has an open area forming a cavity 212 having an inside radius 214 indicated.

The inside radius 214 of support 210 forms the suspended radius of the resonator, and defines the portion of the resonator material which is active and moving. Thus, radius 214 represents the value that is used in calculations of resonant frequency.

Within cavity 212, one or more lower electrodes 220A, 220B are formed on substrate 205. It will be appreciated that lower electrodes 220A and 220B may be formed within substrate 205 directly, and may be formed before or after formation of support 210. Lower electrode 220A, 220B may be segmented into multiple parts as shown (but not limited to two parts), or may consist of a single element (not shown). Lower electrodes 220A, 220B may be driven with different phase electrical signals and may be sensed or detected separately. More than two electrodes may be formed, with some dedicated to a driver alone and some dedicated to a detector alone.

A fluid 230 under test, which generally surrounds the sensor is exposed to, and is in communication with a thin plate 215, having height or thickness 233 as indicated by the dimensioning arrows.

In accordance with one embodiment of the present invention, a direct-current (DC) electrostatic potential is placed between top electrode 225 and lower electrodes 220A, 220B, which causes an in-plane elastic strain to develop in thin plate 215 due to elastic deformation in the plane of thin plate 215. Varying the in-plane elastic strain causes the resonant frequency of thin plate 215 to change. A driving alternating current (AC) electrostatic potential is superimposed on DC potential for electrostatic excitation of thin plate 215 into mechanical resonance. DC potential may then be changed or swept, thus providing variable in-plane elastic strain in thin plate 215, and a plurality of resonant frequencies sensed or measured. Thin plate 215 can remain in mechanical resonance during DC potential sweep, thus a continuum of resonant frequency versus strain is obtained. A plurality of resonant frequency peaks can be detected or measured as a variable DC potential is employed as a tensioner. Resonant frequency may be detected by measuring the varying capacitance between thin plate 215 and lower electrodes 220A, 220B as thin plate vibrates. It will be appreciated that in higher modes of vibration, it may be beneficial to drive, and detect using lower electrode 220A separate from lower electrode 220B.

In accordance with another embodiment of the present invention, a plurality of sensor elements may be incorporated, each held at a distinct DC electrostatic potential while a plurality of resonant frequencies are sensed or detected separately for each sensor element. This embodiment provides substantially instantaneous feedback of changing fluid physical properties such as density and viscosity.

In accordance with another aspect of the present invention, multiple sensor elements may be incorporated, each having distinct physical geometries. A plurality of sensors each having thin plate 215 with different geometrical dimensions (radius 214 and thickness 233) may be driven or excited into resonance in order to provide a plurality of distinct resonant frequencies to determine fluid properties. The effect of geometric changes on resonant frequency behavior differs depending on whether thin plate 215 is in a bending stiffness-dominated regime or a in-plane strain-dominated regime.

It will be appreciated that support 210 can be segmented or contain passages (not shown) to allow fluid 230 into cavity 212 so that fluid 230 communicates with a bottom surface of thin plate 215. Passages (not shown) can also be formed into substrate 205 to allow fluid 230 into cavity 212 so that fluid 230 communicates with bottom surface of thin plate 215. If no passages are formed in support 210 or substrate 205, then bottom surface of thin plate 215 will be in communication with a second fluid occupying cavity 212. Second fluid may be substantially a vacuum, or be characterized by a second viscosity and a second density that are sufficiently small such that second fluid has substantially immeasurable effect on resonant frequencies of said thin plate 215. Second fluid may also be a reference fluid with predetermined values characterized by a second density and a second viscosity such that second fluid has a predictable effect on resonant frequencies of thin plate 215.

Beam Embodiment

Figure 3:
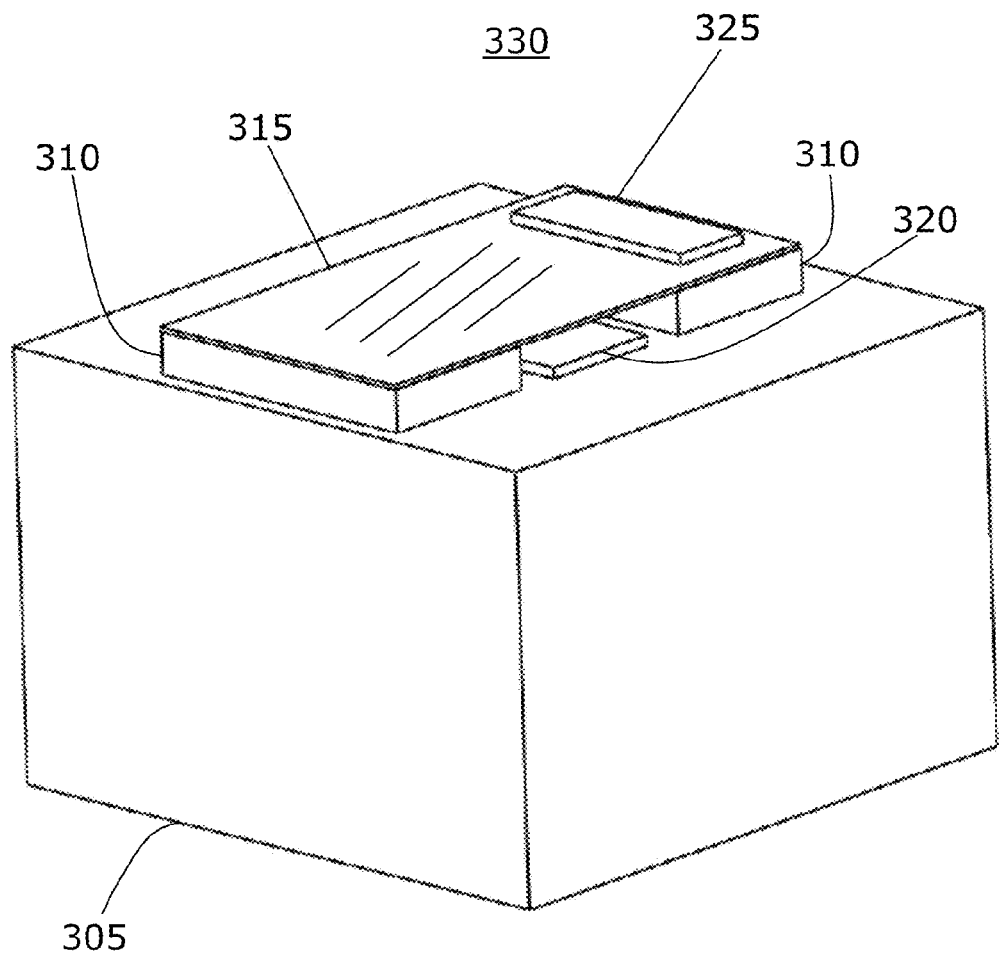
FIG. 3 is a perspective view of an embodiment of the present invention having a beam-shaped resonator.

In another embodiment of the present invention, FIG. 3 illustrates a beam shaped resonator. Substrate 305 is provided with a top or principal surface. End supports 310 are placed onto principal surface of substrate 305. A lower electrode 320 is provided on substrate 305 between end supports 310. A thin plate or beam 315 is provided between end supports 310, and an top electrode 325 is formed onto top surface of thin plate 315 such that top electrode 325 makes electrical contact with thin plate 315. It will be appreciated that in this embodiment, fluid 330 is in direct communication with both a top surface and a bottom surface of thin plate 315 without explicit formation of fluidic passages.

A DC potential is applied between top electrode 325 and lower electrode 320 in the case of a tensioner being employed by electrostatic means for variable in-plane strain. Electrostatic forces between lower electrode 320 and thin plate 315 cause thin plate 315 to stretch and deform slightly to a new equilibrium position, thus imparting in-plane elastic strain (tension) in thin plate 315 that is proportional to applied DC potential. Additionally, a driver is provided by an AC (time-varying) signal or waveform applied between lower electrode 320 and thin plate 315 in the case of electrostatic drive. In the case of a capacitive detector, a time varying capacitance is sensed between lower electrode 320 and thin plate 315.

The shapes presented above in FIG. 1, FIG. 2, and FIG. 3 are not meant to be limiting. The same general principals apply to suspended portions of a thin plate or beam having suspended shape selected from the group consisting of disks, squares, rectangles, beams, and cantilevers.

Flexible or Compliant Supports

Figure 4:
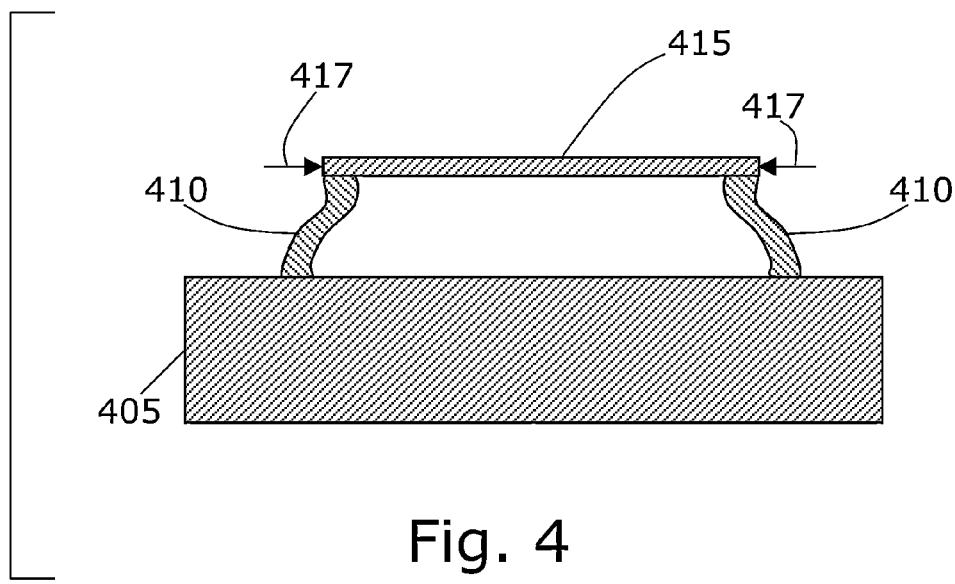
FIG. 4 is a cross-sectional view of an embodiment of the present invention having flexible supports for reducing the quiescent in-plane elastic strain in the thin plate.

In a further embodiment of the present invention, illustrated in FIG. 4 as a cross-sectional view, a technique is employed for controlling the quiescent (without DC potential) in-plane elastic strain. On substrate 405, compliant or flexible supports 410 are provided, which are substantially compliant to allow motion of the top of flexible support 410. Flexible support 410 can be made compliant by having a narrow cross-section, allowing a slight bending from top to bottom. A relaxed thin plate 415 is provided on top surface of flexible support 410, wherein relaxed thin plate 415 exists in a more relaxed state (reduced quiescent in-plane elastic strain) due to the compliance of flexible support 410 and slight lateral shrinking or compressing (as indicated by arrows 417) of relaxed thin plate 415. This allows the use of materials that would otherwise have substantially large quiescent in-plane tensile strain, which would otherwise render operation to be substantially membrane-like. When flexible support 410 is employed, the quiescent strain in relaxed thin plate 415 is lowered to plate-like operation, wherein bending stiffness is significant. It will be appreciated that relaxed thin plate 415 can then be tensioned by a DC potential as described previously, but a starting value of strain at zero DC potential will be lower due to the use of flexible support 410.

Other "spring" structures are known in the art of MEMS, which can be provided in place of or in addition to flexible support 410 in order to allow ends or edges of relaxed thin plate 415 to displace slightly in order to reduce in quiescent strain.

in-Plane Elastic Strain Control by DC Electrostatic Tensioner

Figure 5:
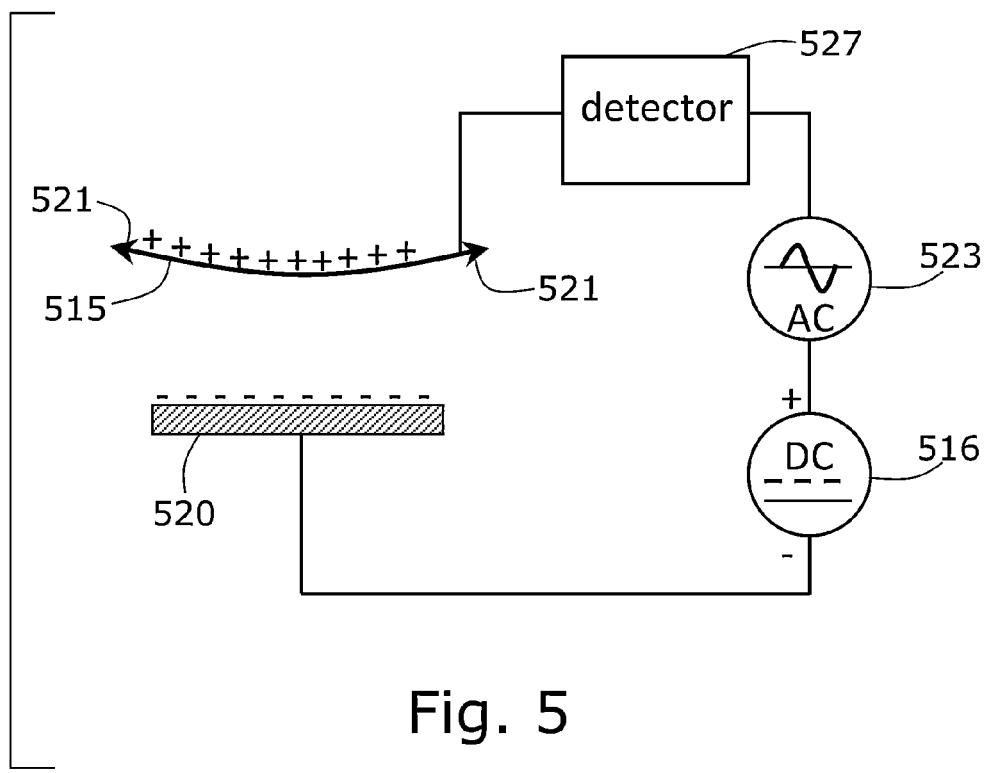
FIG. 5 is a diagram of an embodiment for tensioning a thin plate with a DC electrostatic potential and exciting thin plate with an AC electrostatic potential.

FIG. 5 shows a diagram of an embodiment of a tensioner for providing elastic strain in a thin plate 515 and a driver for exciting thin plate 515 into mechanical resonance. A tensioning DC potential source 516 causes an electrostatic potential difference between thin plate 515 and a lower electrode 520. Electrostatic attractive forces cause thin plate 515 to deflect or deform toward lower electrode 520, elongating or stretching thin plate 515 and defining a new equilibrium position with tensile elastic strain 521 (tensile elastic strain indicated by arrows 521 at ends of thin plate 515) substantially in the plane of thin plate 515. By varying magnitude of DC potential source 516, the magnitude of elastic strain 521 in thin plate 515 can be varied, providing a plurality of resonant frequencies of thin plate 515. In one embodiment, a driver for excitation of thin plate 515 into resonance is provided by electrostatic means. Applying an AC (time-varying) electrostatic potential with AC potential source 523 as a driver provides vibration about an equilibrium position in thin plate 515. Resonance may be achieved in a fundamental or higher mode of vibration by varying frequency of AC potential source 523.

In one embodiment, detector 527 of electrical current provides electrostatic or capacitive sensing of the motion of thin plate 515. Capacitance between lower electrode 520 and thin plate 515 varies as thin plate 515 is excited into resonance and therefore represents a time-varying impedance in the circuit. As electrical quantities are time-varying AC, detector 527 measures a vector quantity including magnitude and phase angle referenced to AC potential source 523, and thereby a detection means is provided.

In-Plane Elastic Strain Control by Support Displacement

Figure 6:
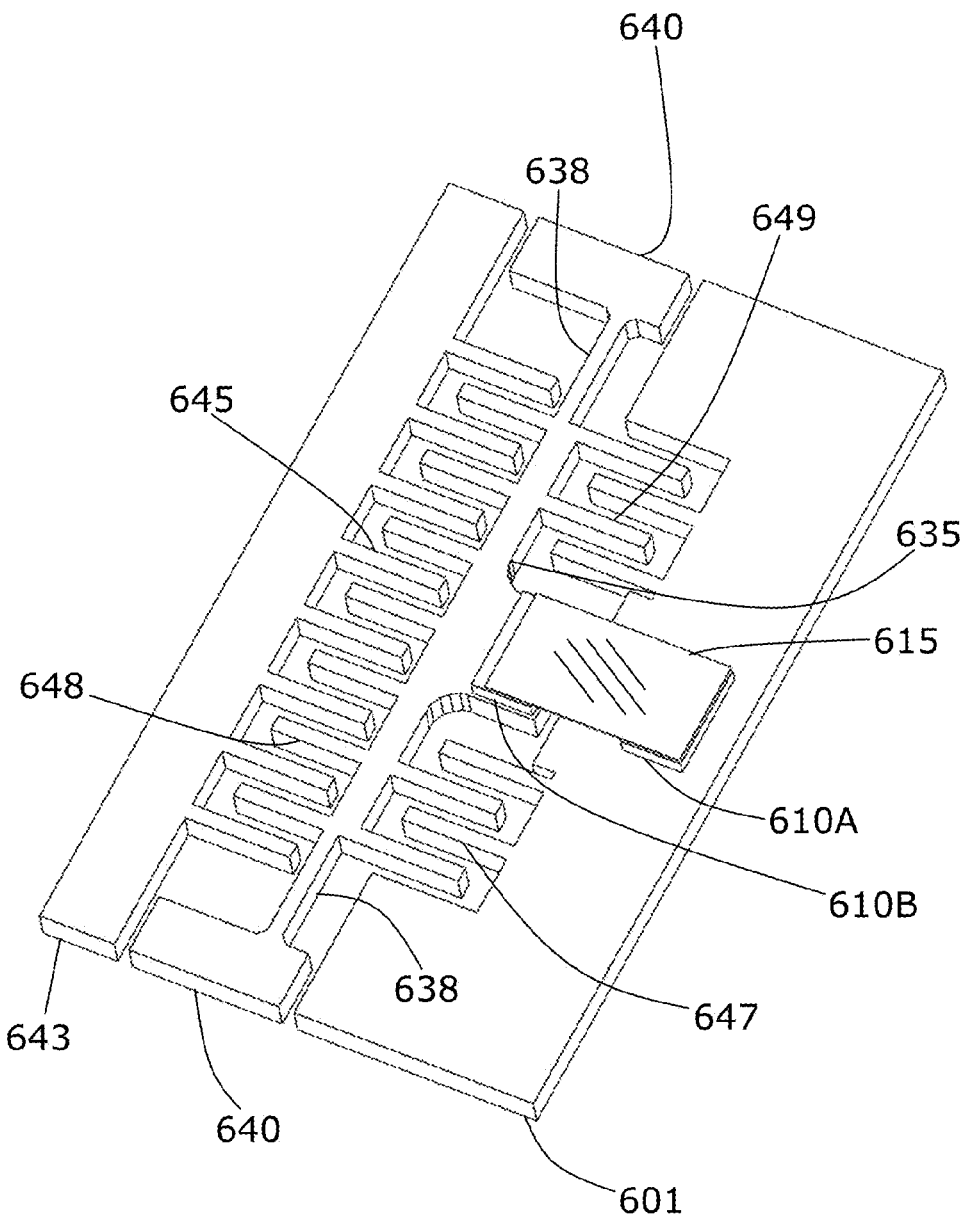
FIG. 6 is a perspective view of an embodiment having a movable, bi-directional comb actuator for controlling the in-plane elastic strain in a thin plate.

In another embodiment of the present invention, a tensioner employing variable in-plane strain and adjustable quiescent strain is depicted in FIG. 6. A device frame 601 is provided with a support 610A positioned on a top surface. A thin plate 615 spans from support 610A to a moving support 610B that is rigidly attached to a moving rack 635. Rack 635 is able to move in the same plane as thin plate 615 through bending of flexures 638. Flexures 638 are anchored to flexure frames 640. A stationary tension frame 643 is provided with stationary tensile comb teeth 645 rigidly affixed thereto. Device frame 601, flexure frames 640 and tension frame 643 remain stationary relative to one another, but electrically isolated from one another. Device frame 601 contains stationary compression comb teeth 647 that are rigidly affixed thereto. Rack 635 is provided with moving tensile comb teeth 648 that interdigitate with, but do not touch stationary tensile comb teeth 645. Rack is further provided with moving compression comb teeth 649 that interdigitate with, but do not touch stationary compression comb teeth 647. Moving tensile comb teeth 648 and moving compression comb teeth 649 are rigidly attached to rack 635, and are in electrical communication with rack 635. Stationary compression comb teeth 647 are in electrical communication with device frame 601. Stationary tensile comb teeth 645 are in electrical communication with tension frame 643.

A tensioner is provided when a DC potential is applied between rack 635 and tension frame 643, whereby electrostatic forces cause rack 635 and moving support 610B to be displaced slightly toward tension frame 643 through bending of flexures 638. This causes thin plate 615 to stretch or elongate slightly and thereby provides an increase in in-plane elastic strain (tension) in thin plate 615.

A DC potential applied between rack 635 and device frame 601 causes rack 635 and moving support 610B to be displaced slightly toward device frame 601 through bending of flexures 638. This causes thin plate 615 to shrink or compress slightly and thereby provides a decrease in in-plane tension in thin plate 615.

It will be appreciated that the structure and operation described in FIG. 6 can be used as a tensioner to provide variable in-plane elastic strain, and also provide control of quiescent strain in thin plate 615 through displacement of at least one support 610B. This embodiment is able to add to, or subtract from quiescent strain to provide a large range of elastic strain values in thin plate 615, and is useful in providing transitions from resonator plate-like behavior (wherein bending stiffness dominates the equilibrium restoring force) to membrane-like behavior (wherein in-plane strain dominates the equilibrium restoring force). The amount of displacement for a typical structure having in-plane dimensions in microns is only on the order of nanometers to produce strain values useful in this embodiment.

The embodiment disclosed in FIG. 6 can be produced from a silicon-on-insulator (SOI) wafer, as is known in the art of MEMS. The device layer of the SOI wafer is patterned and etched to form moving compression comb teeth 649, stationary compression comb teeth 647, moving tensile comb teeth 648, stationary tensile comb teeth 645, rack 635, flexures 638, device frame 601, flexure frames 640, and tension frame 643, preferably in one patterning and etch operation. The moving elements (moving compression comb teeth 649, moving tensile comb teeth 648, rack 635, and flexures 638) are released by etching of the silicon dioxide buried oxide layer (not shown) underneath of moving elements. The remainder of the resonator structure can be fabricated as described in a later section. Suitable SOI wafers for this purpose can be obtained from http://memsengineering.com, for example.

Modes of Vibration

FIG. 7 illustrates a thin plate 715 undergoing a fundamental vibration mode. Thin plate 715 deflects in such a manner that all points on the plane are moved in the same normal direction at any snapshot in time. Fluid 730 must either move substantially normal with deformation of thin plate 715, or move substantially tangential, as indicated by the arrow, to avoid entrainment in the normal motion of thin plate 715. If fluid 730 is viscous, the tangential motion is opposed by the viscosity of fluid 730, and therefore is more predisposed to stay entrained with the normal motion of thin plate 715.

FIG. 8 illustrates a thin plate 815 undergoing a higher mode of vibration, the first radial mode. In this case, roughly half of thin plate 815 is displacing in an upward direction, while the other half is anti-phase, displacing in a downward direction at a snapshot in time. In the case of fluid 830 being inviscid, the effect of the inertia of fluid 830 will be less than in the fundamental mode, since the fluid is free to move tangentially between adjacent segments that are in opposite phase. If fluid 830 is viscous, it is less free to move tangentially compared to the inviscid case, and therefore the difference in entrained mass between an inviscid and viscous fluid 830 is greater in this higher mode. Excitation of this higher mode is provided by driving the sensor with an AC waveform having a higher frequency than in the case of the fundamental mode. Referring briefly to FIG. 2, driving lower electrode 220A apart from lower electrode 220B with an out-of-phase but identical frequency AC waveform is advantageous in achieving this higher mode with an electrostatic driver having a plurality of electrodes.

It will be appreciated that, for example, in the first radial mode of vibration, it would be advantageous to separately detect using lower electrode 220A apart from lower electrode 220B, if capacitive detection is employed, since one half of thin plate 815 represents an increase in capacitance (where thin plate 815 is displaced in a downward direction) while the other half of thin plate 815 represents a decrease in capacitance (where thin plate 815 is displaced in an upward direction). When detection is capacitive, comprising a plurality of electrodes, the separately detected signals may be algebraically combined (by subtraction, in this example) for improved sensitivity.

FIG. 9 illustrates a thin plate 915 in the first non-fundamental circular or circumferential mode of vibration. Fluid 930 is able to move tangentially in a radial direction, restrained by viscous forces, into anti-node segments of vibrating thin plate 915. It will be appreciated that lower electrodes for driving in this mode may be made substantially concentric for optimal operation in this mode, though concentric electrodes are not essential for exciting this mode. Generally, excitation that is required is a specific higher frequency than in the case of the radial mode.

Each mode of vibration has a distinct resonant frequency. By driving to excite multiple distinct modes of vibration, a plurality of distinct resonant frequencies is provided. Different modes provide greater sensitivities to viscosity or to density.

Resonant Frequency Data

Figure 10:
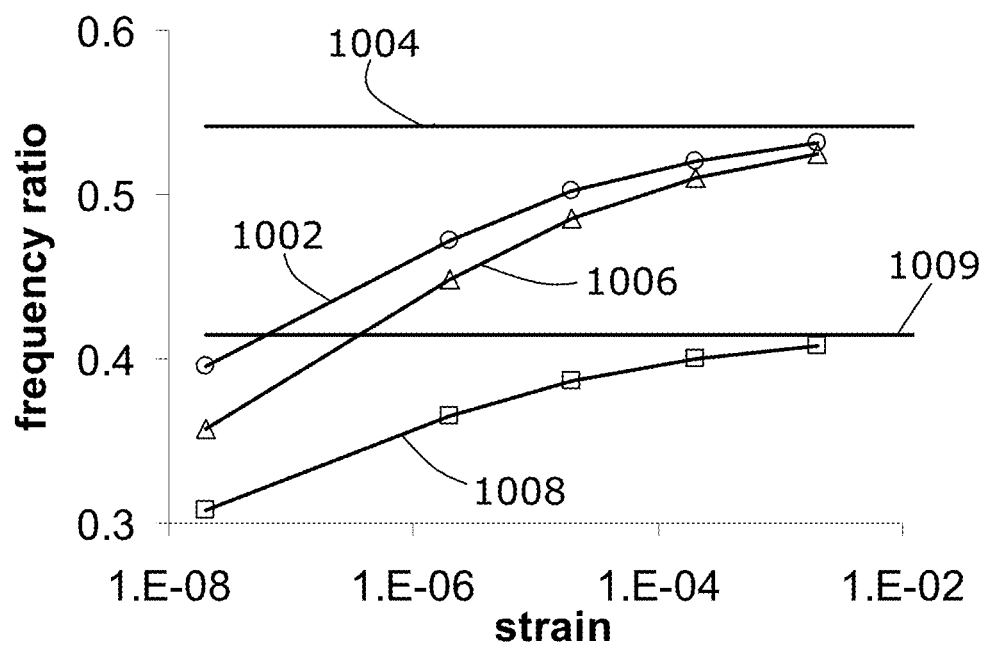
FIG. 10 is a graph of resonant frequency ratio (relative to vacuum resonant frequency) versus in-plane elastic strain in a resonator disk for three different gasses.

A graph of frequency ratio versus dimensionless in-plane strain is illustrated in FIG. 10. Here, frequency ratio is the value of the resonance frequency when operated in a fluid relative to the frequency of the resonator when operated in vacuum. In-plane elastic strain is varied from $2\times10^{-8}$ to $2\times10^{-3}$. Illustrated are frequency responses of three fluids: A gas 1 1002 has viscosity and density similar to that of air at standard temperature and pressure. As the strain is increased in the resonator plate by a tensioner, the plate becomes dominated by strain, the resonant frequency approaches the same value as if gas 1 1002 were inviscid, the inviscid limit 1004. A second gas, gas 2 1006 has the same density as gas 1 1002, but has a higher viscosity. At low values of in-plane strain, the resonator plate is dominated by bending stiffness, and the resonant frequency for gas 2 1006 is lower than that of gas 1 1002 because the viscosity causes more mass to be entrained with the motion of the resonator. As the in-plane strain is increased (for instance, by increasing the DC potential between the resonator plate and the lower electrode or substrate), the resonant frequency increases as the plate becomes more membrane-like, and approaches the same inviscid limit 1004 as for gas 1 1002. Gas 3 1008 has the same viscosity as gas 1 1002 but has a higher density. Because the density is different, there exists a different, lower inviscid limit 1009 for gas 3 1008, due to the higher density.

Solutions to equations (1) and (2) are used to populate a database consisting of density/viscosity relationships for different resonator geometries, modes of vibration, and in-plane strains. Solutions to equations (1) and (2) are alternatively solved in real-time to model the frequency response and provide density and viscosity values. A computer then matches physical properties of fluid to resonant frequencies.

Different techniques can be employed to obtain frequency response data. In one embodiment, a single resonator element has the DC potential varied to sweep the in-plane strain, and the resonant frequency detected or tracked continuously. Resonator can be maintained in resonance during the DC potential sweep. Alternately, a plurality of resonators can be employed, each held at different values of in-plane strain (each with a distinct DC potential), and frequency responses determined for each resonator element, thus providing a plurality of points along a curve for modeling and calculating a best-fit for viscosity/density to frequency versus strain data.

Data is generated for resonators of different dimensions (radius or length, and thickness), shapes, and vibrational modes that can all be incorporated into modeling and fitting routines, databases and algorithms.

Microfabrication Process

Figure 11:
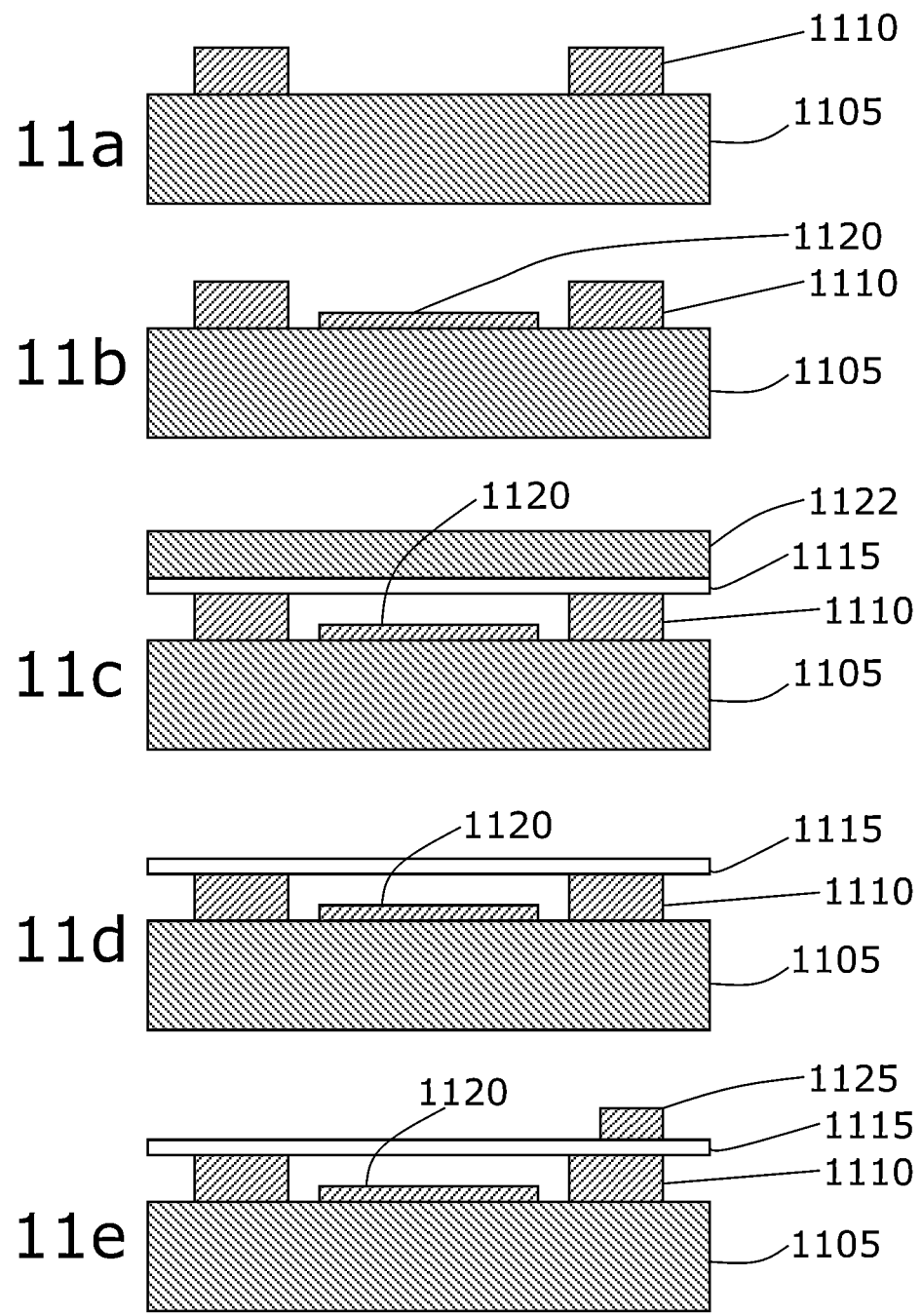
FIG. 11 is a cross-sectional microfabrication sequence for a process of micro-fabricating a sensor element.

FIG. 11 illustrates the steps of a microfabrication sequence for fabricating resonator devices. In FIG. 11a, a substrate 1105 is provided with a support 1110. Support 1110 may be fabricated by a variety of methods known in the art, preferably by depositing a dielectric such as silicon dioxide or silicon, and patterning the shape of support 1110 using standard lithographic techniques and etching dielectric so that dielectric material remains only where support 1110 is desired.

FIG. 11b illustrates the formation of a lower electrode 1120 in the cavity or space between supports. This electrode is electrically conducting, and may be formed by blanket deposition and etch, or by a liftoff technique. The formation of lower electrode 1120 may occur before formation of support 1110, or after. Furthermore, lower electrode may be formed within substrate 1105 as a doped or conductive region of substrate 1105.

In FIG. 11c, a thin plate 1115 is attached to support 1110. For microfabrication, this should occur across the entire wafer in one step. Thin plate 1115 may be attached to a base 1122 for handling and transfer of thin plate 1115 to support 1110. Thin plate 1115 may be made of silicon, graphene, or silicon nitride, among other materials. In the case of graphene, available from https://graphene-supermarket.com/, base 1122 may be made of copper or silicon dioxide. Graphene is an excellent electrical conductor, and therefore requires no other treatment for use as a capacitively-detected, or electrostatically-driven resonator. In the case of single-crystal silicon, base 1122 may be a thicker silicon substrate with a silicon dioxide layer sandwiched between (an SOI wafer, available from http://www.soitec.com/ with thin silicon device layers) wherein the device silicon layer should be made electrically conductive by doping or other means if electrostatic methods are employed for driving or detecting. SOI device layer which forms thin plate 1115 may be further thinned by repeated thermal oxidation and selective silicon oxide etch in hydrofluoric acid, as is known in the art of MEMS. In the case of silicon nitride or poly-silicon used to form thin plate 1115, material is deposited directly onto a silicon substrate. If electrostatic means are used for detecting/driving, an additional conductive layer is needed in the case of an electrically insulating thin plate 1115. Attachment of thin plate 1115 to support 1110 can be achieved by several methods. Equipment for wafer-scale bonding is available from Electron Visions http://evgroup.com and Karl Suss http://www.suss.com/products/wafer-bonder/. Van der Waals forces have been found sufficient for attachment in the case of graphene. For SOI wafer attachment, eutectic (for example: Ge/Al), fusion bonding, or activated surface bonding is suitable, as is known in the art of MEMS sensors.

In FIG. 11d, base 1122 is removed by etching or cleaving, leaving thin plate 1115 suspended over lower electrode 1120 and between supports 1110. The portion of thin plate 1115 between supports 1110 forms the resonator structure.

It will be apparent to those skilled in the art that a suspended structure may be formed by other means. As an alternative example, a sacrificial material may be formed in the cavity between supports 1110. Thin plate 1115 material can then be formed over sacrificial material spanning between supports 1110, for instance, directly by chemical vapor deposition (CVD). Finally, sacrificial material may be etched or removed to release a suspended structure that is functionally the same. Sacrificial etch can be, for example, buffered hydrofluoric acid (HF) or HF vapor if the sacrificial material is silicon dioxide. The advantage to such an approach is in the use of easily deposited materials such as silicon nitride or poly-silicon, which can be deposited in most fabrication facilities by chemical vapor deposition. To achieve high aspect ratios, atomic layer deposition (ALD) can be employed in the formation of thin plate 1115 selected from a large variety of available ALD materials.

Thin plate 1115 having an aspect ratio of 500 is achievable with common materials. For instance, a 40 nanometer thickness of silicon nitride suspended over a 20 micron length has been found robust in processing and in operation. In the case of graphene, a 2 micron length yields an aspect ratio of almost 6000:1, which has also been demonstrated as sufficiently robust in gaseous environments.

FIG. 11e illustrates the formation of a conductive top electrode 1125 onto thin plate 1115. Top electrode 1125 may be formed by blanket deposition, pattern and etch, or by a liftoff or shadowmask process. Alternately, an electrically conductive path can be formed through or around support 1110 to allow circuitry or interconnects within substrate 1105 to be in electrical communication with thin plate 1115.

Measurement Technique

Figure 12:
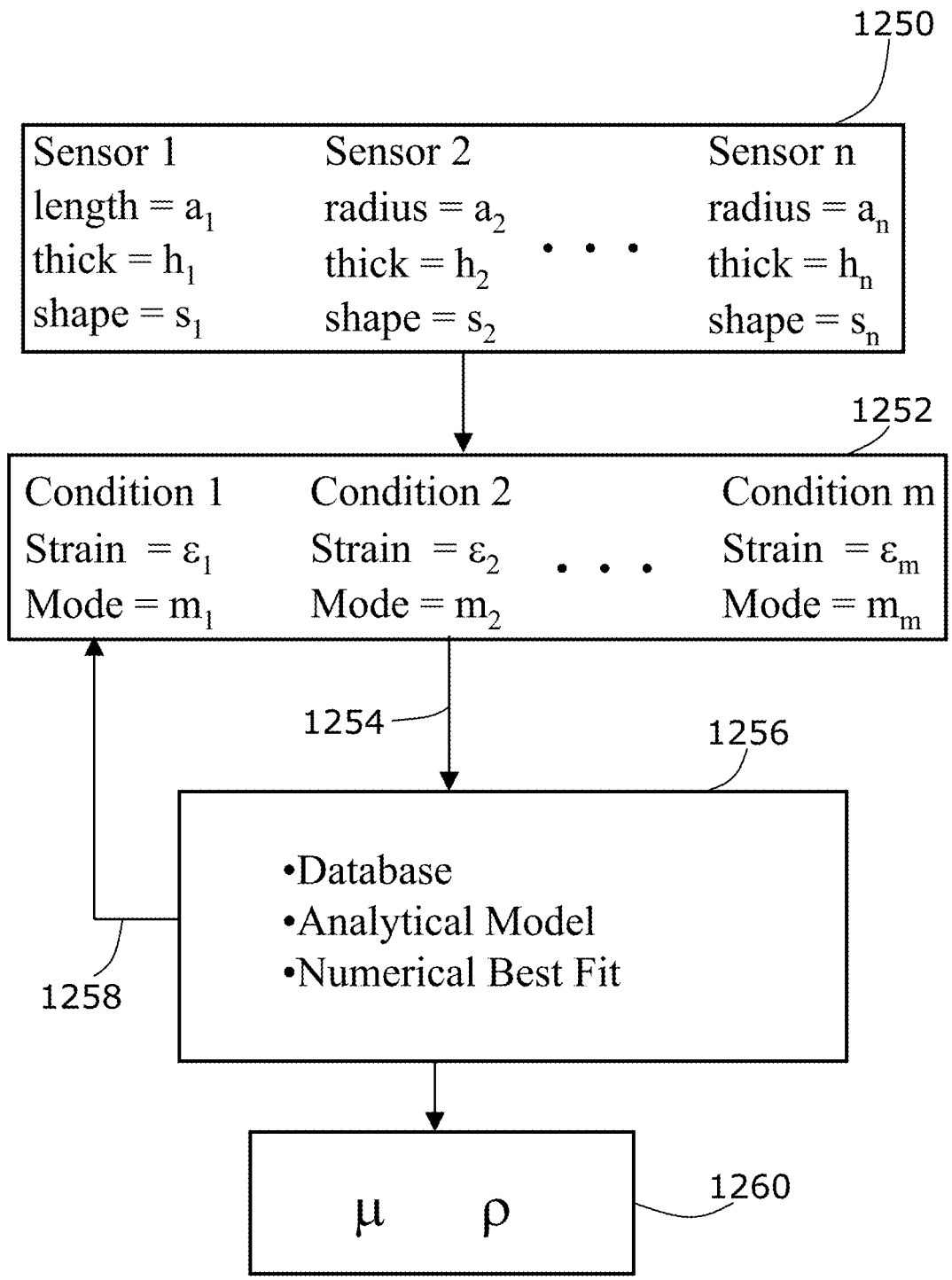
FIG. 12 is a diagram of the measurement approach to obtaining fluid properties from measured resonant frequency peaks.

FIG. 12 is a diagram of the measurement approach to obtaining physical properties of a fluid from measured resonant frequency data. A physical sensor array 1250 is provided. Sensor array 1250 comprises one or more sensing elements consisting of a resonator in communication with fluid, each described by geometrical dimensions (radius or length, thickness or height), and a shape (disk, square, rectangle, beam, cantilever). Each possible geometric combination has equations of motion that describe the motion of the resonator in communication with fluid. Individual resonator element geometric configurations may be repeated, if for instance it is desired to devote particular resonator to always operate in a dedicated mode, or strain.

Each resonator in sensor array 1250 can be operated under different operating conditions 1252. Operating conditions 1252 comprise the vibratory mode of each resonator element, and the amount of in-plane strain induced by tensioning, for example by applying a DC potential. Each physical resonator in sensor array 1250 may be operated in more than one operating condition 1252. Operating conditions 1252 are created by exciting a resonator into mechanical resonance at a plurality of resonant frequencies. Distinct resonant frequencies may be obtained by tensioning resonator to different values of in-plane strain, thereby obtaining a plurality of resonant frequencies.

Detecting is performed such that each resonant frequency of desired combinations of physical resonators in resonator array 1250 and operating conditions 1252 is determined at a plurality of distinct resonant frequencies.

Measured resonant frequency data 1254 comprising detected resonant frequencies of resonator elements is compared to a model or database and provided to a numerical fit algorithm 1256 for calculation of fluid properties. Algorithm 1256 may include a numerical calculation and best-fit method for matching measured resonant frequency data 1254 to an analytical model, or calibration data. Alternately, algorithm 1256 may include a database of cataloged resonator responses obtained by simulation, pre-calculation, analytical models or calibration to compare and match measured resonant frequency data 1254 to values of fluidic properties. Algorithm 1256 compares detected or measured resonant frequency data 1254 to analytical model or database for calculating a best numerical fit of measured resonant frequency data 1254 to model or database.

To obtain higher accuracy or more detailed information, feedback 1258 from algorithm 1256 may be used to request new and different operating conditions 1252, and additional measurements provide new or updated measured resonant frequency data 1254 to algorithm 1256.

Once algorithm 1256 has calculated a suitable best numerical fit or model, numerical results 1260 comprising values for fluid density and viscosity describing fluid are obtained and displayed or transmitted.

In accordance with another embodiment of the present invention, other methods than electrostatic means may be used to excite and detect resonating elements. For instance, Laser Doppler Vibrometry (LDV) can be used to provide both excitation and detection for the resonator element.

Measurement System

Figure 13:
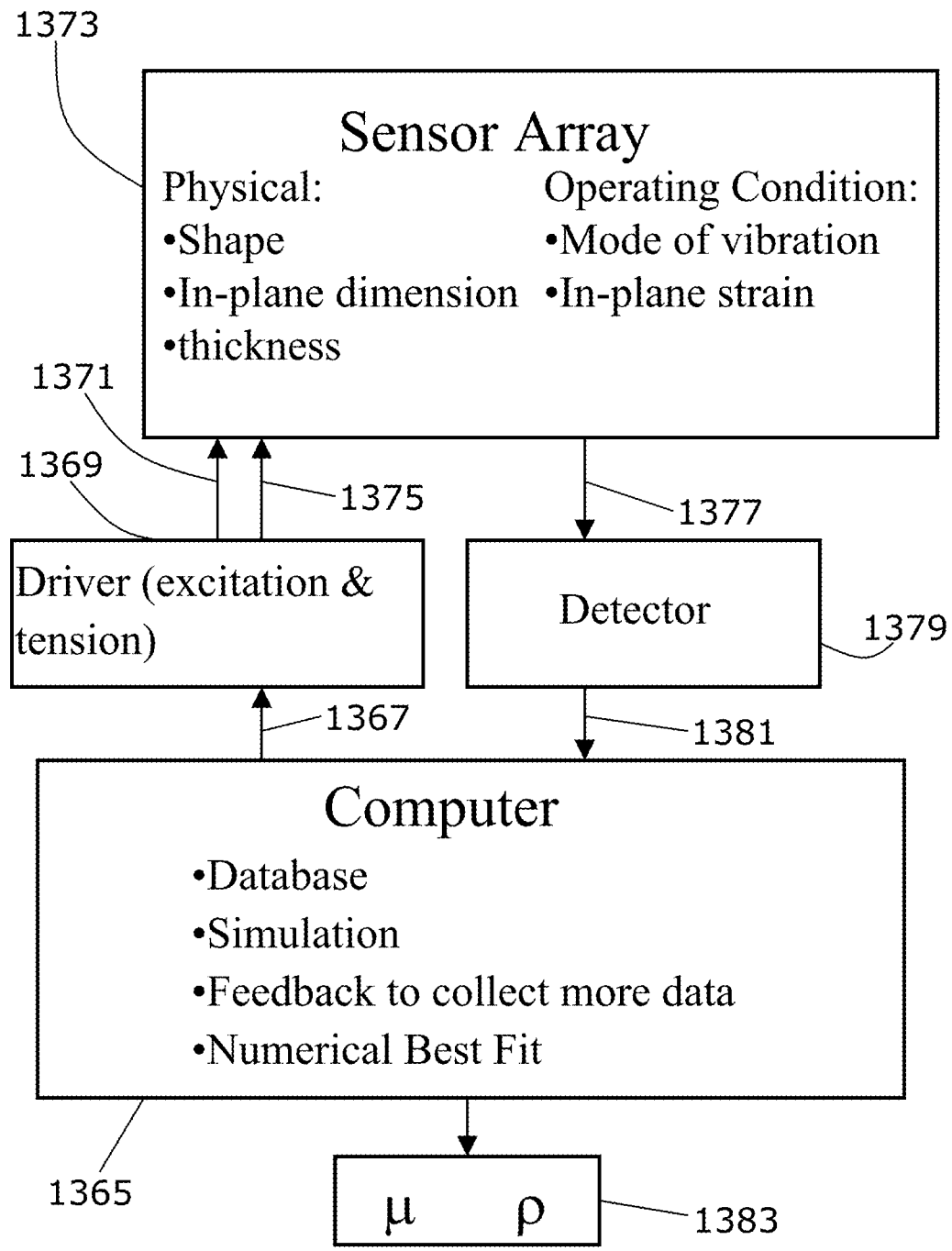
FIG. 13 is a block diagram showing a system used for measuring fluid properties.

FIG. 13 is a block diagram showing a system used for measuring fluid properties. A computer 1365 is provided, which issues commands 1367 to driver 1369. Driver 1369 includes a tensioner to first provide tensioning information 1371 to control the DC potential or strain applied to each physical resonator element that is in communication with a fluid (and possibly reference resonators not in communication with fluid), in a sensor platform 1373. Additionally, driver 1369 supplies necessary excitation signals 1375 to excite each resonator in one or more modes of vibration at a plurality of distinct resonant frequencies. Excitation signals 1375 are AC, or time varying waveforms that drive each resonator element to mechanical resonance, which may be a fundamental mode of vibration or a higher mode of vibration.

Sensor platform 1373 comprises the array of resonator elements in communication with fluid, each described by geometrical dimension (radius or length, thickness or height), and a shape (disk, square, rectangle, beam, cantilever). Sensor platform 1373 receives tensioning information 1371 and excitation signals 1375 from driver 1369, which causes physical resonator elements in 1373 to be in mechanical resonance under different operating conditions.

Motion data 1377 is provided by sensor platform 1373 to detector 1379. Detector 1379 determines distinct resonant frequencies from each resonator element in sensor platform 1373 under each operating condition created by tensioning information 1371 and excitation signals 1375. Measured resonant frequency data 1381, comprising a plurality of distinct resonant frequencies, is transmitted to computer 1365.

Computer 1365 receives measured plurality of distinct resonant frequency data 1381, and contains a computer program that instructs computer 1365 with a fitting means for data analysis and calculating a best-fit for matching physical properties of fluid to measured frequency data 1381. Algorithm may include a numerical calculation and best-fit method for matching measured resonant frequency data 1381 to an analytical model, or calibration data. Alternately, computer 1365 may include a database of cataloged resonator responses obtained by simulation, pre-calculation, analytical models or calibration to match measured resonant frequency data 1381 to values of fluidic properties. Fitting means can include a method of least-squares or similar known method.

Computer 1365 may determine that higher resolution or accuracy is needed, or a different measurement scheme may be beneficial. Computer 1365 may then request a new set of measurements by issuing a new set of commands 1367 to driver 1369, thus forming a feedback loop for obtaining optimal results from the measurement system.

Once computer has determined that the best possible measurement is made with the sensor platform 1373 provided, computer 1365 then transmits or displays the determined fluidic properties 1383.

The invention claimed is:

1. A sensor for measuring physical properties of a fluid comprising:
   a substrate having a principal surface;
   at least one support placed onto said principal surface of said substrate;
   at least one plate suspended from said support and in communication with said fluid wherein said plate is substantially free to oscillate in a direction normal to said plate;
   a driver for exciting said plate into mechanical resonance at a plurality of distinct resonant frequencies;
   a detector for determining said distinct resonant frequencies of said plate;
   a computer for matching said physical properties of said fluid to said distinct resonant frequencies;
   a tensioner for providing variable in-plane elastic strain in said plate;
   whereby said plate is acted on by said fluid and said resonant frequencies are detected and said physical properties of said fluid are determined.

2. The sensor recited in claim 1 wherein said tensioner is an electrostatic potential applied between a lower electrode and said plate.

3. The sensor recited in claim 2 wherein said plate has an aspect ratio greater than 500.

4. The sensor recited in claim 2 wherein said plate is composed of graphene having a thickness of approximately 0.2 to 0.5 nanometer.

5. The sensor recited in claim 4 wherein said in-plane elastic strain is varied from $2 \times 10^{-8}$ to $2 \times 10^{-3}$.

6. The sensor recited in claim 1 wherein said driver excites a plurality of said plates having different geometric dimensions.

7. The sensor recited in claim 1 wherein said tensioner provides a displacement of at least one said support.

8. The sensor recited in claim 1 wherein said support is substantially compliant providing reduced quiescent in-plane elastic strain in said plate.

9. The sensor recited in claim 1 wherein said driver excites a plurality of distinct modes of vibration of said plate.

10. The sensor recited in claim 1 wherein said fluid is in communication with a top surface of said plate and said fluid is in communication with a bottom surface of said plate.

11. The sensor recited in claim 1 wherein said fluid is in communication with a top surface of said plate and wherein a bottom surface of said plate is in communication with a second fluid characterized by a second density and a second viscosity, said second fluid having a predictable effect on said resonant frequencies of said plate.

12. The sensor recited in claim 1 wherein said plate has a suspended shape selected from the group consisting of disks, squares, rectangles, beams, and cantilevers.

13. The sensor recited in claim 1 wherein said driver is electrostatic.

14. The sensor recited in claim 13 wherein said driver further comprises a plurality of electrodes.

15. The sensor recited in claim 1 wherein said detector is capacitive.

16. The sensor recited in claim 15 wherein said detector further comprises a plurality of electrodes.

17. A system for measuring physical properties of a fluid comprising:
   at least one resonator in communication with said fluid;
   a driver for exciting said resonator in one or more modes of vibration at a plurality of distinct resonant frequencies;
   a tensioner for varying in-plane elastic strain in said resonator;
   a detector for determining said plurality of distinct resonant frequencies of said resonator;
   a computer for receiving said plurality of distinct resonant frequencies data from said detector;
   a computer program for instructing said computer in calculating a best-fit for matching said physical properties of said fluid to said plurality of distinct resonant frequencies,
   whereby said physical properties of said fluid can be determined from said plurality of distinct resonant frequencies.

18. A method for measuring density and viscosity of a fluid comprising:
   providing at least one resonator in communication with said fluid;
   exciting said resonator into mechanical resonance at a plurality of distinct resonant frequencies;
   tensioning said resonator for variable in-plane elastic strain in said resonator;
   detecting said plurality of distinct resonant frequencies of said resonator;
   comparing said plurality of distinct resonant frequencies to a model or database;
   calculating a best numerical fit of said plurality of distinct resonant frequencies to said model;
   obtaining said density and viscosity values describing said fluid from said best numerical fit.

* * * * *